United States Patent
Nikinmaa et al.

(10) Patent No.: US 12,263,349 B2
(45) Date of Patent: Apr. 1, 2025

(54) METHOD OF TREATMENT OF BIOLOGICAL SURFACES

(71) Applicant: Koite Health Oy, Espoo (FI)

(72) Inventors: Sakari Nikinmaa, Espoo (FI); Juha Rantala, Espoo (FI)

(73) Assignee: Koite Health Oy, Espoo (FI)

( * ) Notice: Subject to any disclaimer, the term of this patent is extended or adjusted under 35 U.S.C. 154(b) by 310 days.

(21) Appl. No.: 17/288,231

(22) PCT Filed: Oct. 28, 2019

(86) PCT No.: PCT/FI2019/050769
§ 371 (c)(1),
(2) Date: Apr. 23, 2021

(87) PCT Pub. No.: WO2020/084199
PCT Pub. Date: Apr. 30, 2020

(65) Prior Publication Data
US 2021/0387013 A1   Dec. 16, 2021

(30) Foreign Application Priority Data

Oct. 26, 2018   (FI) ...................................... 20185904

(51) Int. Cl.
*A61N 5/06*   (2006.01)
*A61K 41/00*   (2020.01)

(52) U.S. Cl.
CPC .......... *A61N 5/062* (2013.01); *A61K 41/0057* (2013.01); *A61N 5/0603* (2013.01);
(Continued)

(58) Field of Classification Search
CPC .... A61N 5/062; A61N 5/0603; A61N 5/0616; A61N 5/0624; A61N 2005/0606; A61N 5/06; A61K 41/0057
See application file for complete search history.

(56) References Cited

U.S. PATENT DOCUMENTS

2002/0165594 A1   11/2002   Biel
2002/0183808 A1   12/2002   Biel
(Continued)

FOREIGN PATENT DOCUMENTS

CA   2948258 A1   1/2011
CN   1771073 A    5/2006
(Continued)

OTHER PUBLICATIONS

Jiang et al: Toluidine blue O and porphyrin-mediated photodynamic therapy on three main pathogenic bacteria of periodontitis using portable LED phototherapy device. Journal of Innovative Optical Health Science, 2015, vol. 8, No. 4.
(Continued)

*Primary Examiner* — Jonathan T Kuo
(74) *Attorney, Agent, or Firm* — Laine IP Oy; Mark W. Scott

(57) ABSTRACT

Method of treating biological surfaces with electromagnetic radiation in the form of light of two different energy levels, a first light with photons having a majority energy in the range from 3.5 eV to 2.8 eV and a second light with photons having a majority energy in the range from 1.24 eV to 2.48 eV. The photons of the first light and the second light are simultaneously directed against the biological surface. The invention also contemplates the use of sensitizers in topical treatments of infections using the method. The treatment will achieve good tissue penetration. It makes it possible to give antibacterial treatment to different areas of pathogen at the same time as two or more different energy photons can target molecules in different areas.

33 Claims, 4 Drawing Sheets

(52) U.S. Cl.
CPC ......... *A61N 5/0616* (2013.01); *A61N 5/0624* (2013.01); *A61N 2005/0606* (2013.01)

(56) References Cited

U.S. PATENT DOCUMENTS

| | | |
|---|---|---|
| 2003/0059379 A1 | 3/2003 | Andersen et al. |
| 2004/0052798 A1 | 3/2004 | Neuberger |
| 2004/0193235 A1* | 9/2004 | Altshuler ............ A61N 5/0603 607/88 |
| 2005/0059731 A1 | 3/2005 | Albrecht et al. |
| 2006/0093561 A1 | 5/2006 | Kennedy |
| 2006/0281042 A1* | 12/2006 | Rizoiu ................ A46B 7/04 433/29 |
| 2008/0255498 A1* | 10/2008 | Houle ............... A61C 17/0208 604/20 |
| 2010/0100030 A1 | 4/2010 | Driscoll et al. |
| 2012/0088204 A1 | 4/2012 | Ho et al. |
| 2012/0095059 A1* | 4/2012 | Rosado ................. A61K 31/44 514/342 |
| 2012/0245506 A1 | 9/2012 | Piergallini et al. |
| 2016/0016001 A1 | 1/2016 | Loupis et al. |
| 2017/0157254 A1 | 6/2017 | Piergallini et al. |
| 2021/0030874 A1* | 2/2021 | Pätilä ................ A61K 31/7052 |
| 2022/0167853 A1* | 6/2022 | Nikinmaa ............ A61B 5/0071 |

FOREIGN PATENT DOCUMENTS

| | | |
|---|---|---|
| CN | 2875367 Y | 3/2007 |
| CN | 102725024 A | 10/2012 |
| CN | 204302166 U | 4/2015 |
| JP | 2010284399 A | 12/2010 |
| WO | WO2006135344 A1 | 12/2006 |
| WO | WO2011006263 A1 | 1/2011 |
| WO | WO2011084746 A1 | 7/2011 |
| WO | WO2017019836 A1 | 2/2017 |
| WO | WO2017070155 A1 | 4/2017 |

OTHER PUBLICATIONS

Tavares et al: Antimicrobial photodynamic therapy alone or in combination with antibiotic local administration against biofilms of Fusobacterium nucleatum and Porphyromonas gingivalis. Journal of Photochemistry and Photobiology B Biology, Sep. 12, 2018, vol. 188, pp. 135-145.

* cited by examiner

METHOD OF TREATMENT OF BIOLOGICAL SURFACES

FIELD OF INVENTION

The invention relates to anti pathogen treatment of biological surfaces. In particular, the invention relates to a method of treating surfaces by photodynamic therapy.

BACKGROUND

In biofilms microorganism are less susceptible to antimicrobials than bacteria in planktonic form. The mechanism behind the tolerance and resistance in biofilms includes slow penetration of antimicrobials through the biofilm matrix, altered microenvironment within the biofilm, different stress response of bacterial cells and the formation of sub-populations of so-called persister cells. In biofilms, potential resistance can be easily transferred among different species by horizontal gene transfer. It has been estimated that close to 80% of all microbial infections are caused by biofilms. This also relates to drug resistance where susceptible pathogen strains acquire resistance and selection of inherently less susceptible species make population more resistant.

Frequent biofilm infections include dental infections caused by dental plaque, as well as dermal infections, urinary tract infections, middle-ear infections, endocarditis and implant- or catheter-associated infections.

Successful antimicrobial treatment of microorganism in biofilms typically requires up to 100 to 1000 times higher concentrations of disinfectants or antibiotics than when treating their planktonic counterparts. For example, in a test, a 100 time greater concentration of amine fluoride and chlorhexidine was needed to kill monospecies biofilm of *Streptococcus sobrinus* than its planktonic counterpart. Similarly, *Escherichia coli, Pseudomonas aeruginosa* and *Staphylococcus aureus* required the application of 1000 time higher concentrations of antibiotics for effective treatment in biofilm compared to their planktonic form.

Dentists often have to combat antibiotic-resistant bacteria in periodontal or endodontic infections. It has been observed that resistance against disinfectants like chlorhexidine, the most common tool of dentists to treat oral infections, may correlate with antibiotic resistance.

Antibiotics have helped man to cope with bacterial infections to date, but the pathogens have become resistant to most of the antibiotics and the difficulty to develop new antibiotics threatens to return mankind to the pre-antibiotic era.

New antimicrobial strategies are therefore needed for example in dentistry in order to avoid excessive usage of antibiotics for treatment of periodontal, endodontic or mucosal topical infections caused by bacterial or yeast biofilms.

SUMMARY OF THE INVENTION

It is an aim of the present invention to provide methods of antimicrobial treatment while decreasing the risk of developing resistance in pathogens.

In particular, it is an aim to provide an approach for treating biological surfaces primarily by using light.

The present invention is based on the idea of treating biological surfaces with a combination of high and low energy photons simultaneously. It has surprisingly been found that the simultaneous use of high and low energy photons on the target area of a surface will give a biocidal effect that is better than the use of such photons separately.

It would appear—although this is merely one possibility, and the scope of the present invention is not limited to the following explanation—that low energy photons will penetrate deep into the surface, such as tissue, causing a heating effect, whereas high energy photons will have a biocidal effect on the surface. Thus, low energy photons upon absorption by the tissue will have a tissue heating effect of more than 1° C., for example 1.5 to 3.5° C., such as 2.7° C., up to a depth of about 2 cm. In live (i.e. blood-filled) tissue, this would seem to increase the oxygen partial pressure and blood circulation that subsequently stimulates the metabolism of the cells and potentially promotes immune reactions. High energy photons, for example having an energy level of twice that of the low energy photons, have an endogenous bacteria killing effect although the depth to which the photons penetrate into the tissue is smaller than for the low energy photos.

Thus, the same target area can be activated through photon up-conversion reactions where two or more photons are simultaneously absorbed and cause the target molecule(s) to excite to a higher energy state.

In one embodiment, a method is provided wherein the target area is contacted with a photosensitizer and then the target area thus treated will be subjected to the combination of first photons having a majority energy between 1.24 eV and 1.65 eV and second photons having a majority energy between 2.8 eV and 3.5 eV, said first and said second photons making up a majority, preferably more than 90%, of all photons directed towards the target area.

A further embodiment provides a photosensitizer for use in the topical treatment of an infection on a mammal, wherein said sensitizer is applied to a part of skin or mucous membrane and that part is subsequently or simultaneously subjected to first photons with a majority energy between 2.8 eV and 3.5 eV; and second photons with a majority energy between 1.24 eV and 1.65 eV.

In one embodiment, a photosensitizer is provide for use in topical treatment of an infection on a mammal, wherein said sensitizer is first applied to a part of the skin or mucous membrane and that part is subsequently or simultaneously subjected to photons with a majority energy between 3.17 eV and 2.95 eV and 1.56 eV and 1.45 eV, respectively. Such energy levels correspond to wave lengths of about 390 to 420 nm and 795 to 855 nm, respectively.

A still further embodiment provides a kit for treatment of microbial, viral or fungal infections of tissue, in biofilm, saliva, skin, plaque, on teeth surfaces and in mucous membranes, comprising an optoelectronic component and device thereof capable of simultaneously emitting a first light consisting of high energy and a second light consisting of low energy photons, said first and said second light amounting to at least 80% of all light emitted from the optoelectronic component or device, and at least one photosensitizer which can be activated by at least either of the high energy and low energy photons.

More specifically, the present invention is characterized by what is stated in the independent claims.

Considerable advantages are obtained. The use of high and low energy photons to target endo- and exogenous molecules gives rise to a target molecule site specific treatment due to low life-time of reactive or high energized oxygen.

According to the invention the high energy photons are being absorbed by endogenous (intracellular) molecules to generate reactive oxygen singlets and reactive oxygen.

Simultaneously low energy photons are being absorbed exogenously (extracellular) by the photo-sensitizer resulting in reactive oxygen singlets and reactive oxygen. The reactive oxygen singlets and reactive oxygen species will inactivate, kill and otherwise reduce micro-organisms such as bacteria, virus and fungus in tissue, biofilm, saliva, skin, plaque and teeth surface.

The treatment will achieve good tissue penetration. It makes it possible to give antibacterial treatment to different areas of pathogen at the same time as two or more different energy photons can target molecules in different areas. Different energy photons have also different tissue therapeutic and tissue stimulating effects. The combined high and low energy photons can affect bacterial communication as they might have deleterious effect in bacteriophages, which contain genetic material or other molecules. The light may also have effects in the production, formation or activating of such communicating molecules assessed as quorum sensing.

It appears that the high energy photons are typically being absorbed by species relating to or involved with the intracellular oxidative stress responses. They are therefore capable of disrupting pathogen treatment adaptation. One example of such a species is the flavin group of the peroxidase enzyme.

The high and low energy photons can be used with several different kinds of photosensitizers, wherein the activation can take place through different mechanisms such as heat generation, oxygen radicals and singlet oxygen. By utilizing treatment combination where pathogens are targeted with two or more unspecific yet fundamentally different mechanisms, efficient antibacterial treatment can be achieved. In one embodiment, ICG with low energy photons is used with high energy photons to give photo hyperthermia therapy (ICG acts 80% through heat generation and 20-15% through singlet oxygen formation) to pathogen membranes. High energy photons can be used for activating endogenous porphyrin molecules inherent in bacteria. Such molecules have high quantum yields and act mainly through singlet oxygen, resulting in localized oxidative bursts.

One important benefit of the combination of endogenous antibacterial therapy, in which the photons target inherent bacteria molecules, with exogenous photodynamic or photothermal therapy is that it can solve the issue that added exogenous photosensitizers tend to bleach out from target area during treatment.

However, endogenous antibacterial light therapy is not limited to the presence of an exogenous photosensitizer.

Targeting the endogenous molecules inherent in bacteria with photons gives an effect which is independent of the photosensitizer attachment and uptake. This helps to balance the treatment so that areas with less photosensitizer will have as good treatment as the areas with more photosensitizer. The photo bleaching effect of endogenous antibacterial therapy to pathogen endogenous molecules has also antipathogenic function as these molecules are essential for the pathogen unlike the added exogenous photosensitizer.

In long term, the targeting of bacteria endo- and exogenously gives the best effect in vivo against many bacteria as effectivity of exogenous treatment is limited to photosensitizer attachment and/or intake to target pathogen.

For example, simultaneously absorbing 1.53 eV and 3.06 eV photons can excite endogenous porphyrins creating antibacterial effect in addition to tissue healing effect. The high energy photons reduce the formation of biofilm extracellular polysaccharides matrix which gives synergies with exogenous PDT and reduces pathogenicity of biofilms.

Different photosensitizer, photon energy and treatment parameters can be used to target different age biofilms in different part of its life cycle. The composition of, for example dental plaque and biofilms varies from individual to individual. People with low incidence of caries show different bacterial amounts, different species and different phylogenetic diversity within the dental plaque, when compared to the high incidence of caries especially in the early days of plaque formation.

With the present invention people can be efficiently treated, irrespective of whether they are of high or low caries incidence.

The present treatment can also be used for treating other than biological materials having biological surfaces. Examples include equipment and parts of equipment covered by biofilms. Biofilms, also referred to as biofouling, can be found generally in industrial water systems, in the medical and process industries, including the paper and pulp industry, as well as in the food industry.

Next embodiments will be examined in more detail with reference to the attached drawings.

EMBODIMENTS

Definitions

Figure 1:
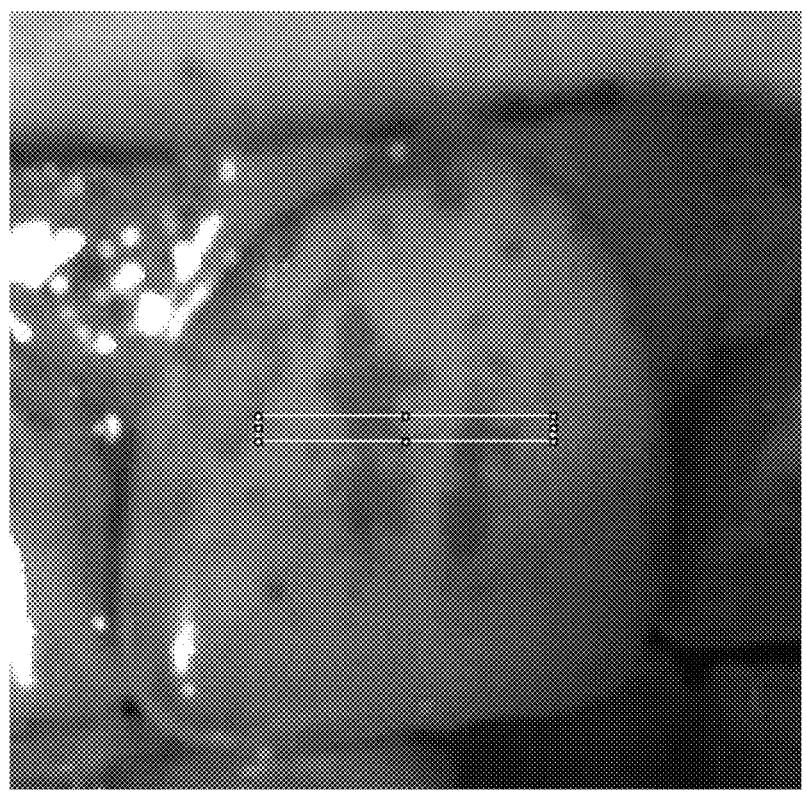
FIG. 1 is a photograph showing dye plaque specificity as observed in room light with hamamatsu 1394 and NIR light source.

In the present context, "photodynamic therapy", also referred to by the abbreviation "PDT", stands for any therapy where light is converted to some form of reactive oxygen.

Examples of "reactive oxygen" includes singlet oxygen, oxygen radicals and oxygen ions.

"Antimicrobial photodynamic therapy", also referred to by the abbreviation "aPDT", is a photochemistry-based method that uses photons to activate "sensitizers" that, in the activated state, impart antimicrobial effect.

In one embodiment, "antimicrobial photodynamic therapy" stands for "antibacterial photodynamic therapy".

In one embodiment, "antimicrobial photodynamic therapy" stands for "antifungal photodynamic therapy".

In one embodiment, "antimicrobial photodynamic therapy" stands for "antiviral photodynamic therapy".

"Benefit agents" are typically chemical compounds or substances which have a beneficial effect on the tissue or treatment effect. Such compounds are exemplified by the following: host defense peptides, enzymes, hydrogen oxide producing enzymes, certain pH liquid, acid, base, antibacterial enzymes, honey, hydrogen peroxide, resin, Trolox, EDTA, D-vitamin, antigens, hormones, prolactin, hydroscopic material, alpha tocopherol, verapamil, sodium bicarbonate, sodium chlorite, pomegranate, aloe vera, chamomile, curcumin, aquacumin, baking soda, sea salt, turmeric, activated charcoal, lemon juice, coconut oil pulling, peppermint oil, spearmint oil, cinnamon oil, DMSO, titanium dioxide, calcium carbonate, carrageenan, sodium lauryl sulfate, sodium monofluorophosphate, benzyl alcohol, *Mentha piperita* oil, *Petroselinum sativum* oil, sodium benzoate, bromelain, papain, maltodextrin, citric acid, Limonene, silica, *Mentha piperita* extract, glycerin, nettle extract, bicarbonates.

"Antimicrobial blue light", also referred to by the abbreviation "aBL", is light, typically in the wave length area of 400 nm to 470 nm, such as 400 nm to 430 nm or 405 to 470 nm, or 405 to 430 nm, that exhibits for example intrinsic antimicrobial effect without the involvement of exogenous photosensitizers.

"Photosensitizers" are compounds or molecules that are capable of absorbing electromagnetic radiation for example in the ultraviolet or visible region and transferring it to adjacent molecules. Typically, the photosensitizers have de-localized π systems.

Although the term "photosensitizer" at instances is used in the singular voice in the present context, the term also comprises several compounds or molecules. In particular it comprises mixtures or sequential use of two or more photosensitizer compounds or molecules. In case of using a plurality of photosensitizer compounds or molecules, at least one is suitable for use with high energy photons and at least one is suitable for use with low energy photons.

In one embodiment, one photosensitizer selected is capable of achieving endogenous antimicrobial action in combination with the corresponding light, and one photosensitizer is selected which is capable of achieving exogenous antimicrobial action in combination with the corresponding light.

The photosensitizers can be naturally occurring compounds ("natural photosensitizers") and synthetic compounds. Examples of natural photosensitizers include the following: Hypericin, curcumin, phenalenone derivatives, Cercosporin, psoralen, xanthotoxin, Angelicin, alpha-Terthienyl, Phenylthepatriyne, THC, Cannabidiol (CBD). Synthetic photosensitizers include the following: RB (Rose Bengal), MB, Porphyrin derivatives, Curcumin derivatives, Methylene Blue, Indocynine Green, Erythosine, Phenalenone derivatives, Fullerene derivatives, Xanthene derivates, Resveratrol.

Other photosensitizers are represented by berry extracts, such as lingonberry and blueberry including polyphenolic compounds and/or anthocyanine compounds.

The term "potentiating substances or agents" stands for agents which are capable of enhancing the effect or activity of other agent(s) so that the combined effect of them is greater than the sum of the effects of each one alone.

Examples of "potentiating substances or agents" includes ions, ion scavengers, surfactants, oxygenated compounds, reactive oxygen producing compounds, organic and inorganic salts, divalent ions, pigments, antimicrobial peptides, EDTA, immunostimulants and antibiotic or other antimicrobial compounds described but not limited to chlorhexidine.

"Exogenous" when used in relation to bacteria stands for "outside" of the bacteria "Endogenous" stands for "inherently present" in the bacteria. When used with reference to molecules and substances in the bacteria, "endogenous" is used interchangeably with the term "intracellular".

In the present context, "mammals" have the conventional meaning in the art. Particularly interesting targets are humans and animals kept for husbandry and as pets, including dogs, cats, rabbits, horses, cattle, sheep, goats and pigs.

"Non-coherent" when used in connection to light means that the amplitude and phase of the emitted light waves fluctuate randomly in space and time. One embodiment comprises using LEDs as non-coherent light sources. Another embodiment comprises using UVC lamps as non-coherent light sources.

"High energy photons" are photons with energy in the range from 3.5 eV to 2.8 eV, in particular about 3.2 to 2.9 eV or 3.17 to 2.95 eV. Typically, such photons are contained in light having a wavelength in the range of about 350-450 nm, for example about 380 to 430 nm, such as 390 to 410 nm.

"Low energy photons" are photons with energy in the range from 1.24 eV to 2.48 eV, in particular 1.3 to 2.4 eV, for example 1.4 to 1.6 eV or 1.45 to 1.56 eV. Typically, such photons are contained in light having a wavelength in the range of about 500 to 1000 nm, for example about 780 to 830 nm Light with photons having "a majority energy in the range from 3.5 eV to 2.8 eV" stands for light, for example in the form of a light beam or light ray, in which at least 50%, in particular at least 60% or at least 70% or at least 80% or at least 90% or at least 95%, of the photons—as indicated by their energy—have an energy in the range from 3.5 eV to 2.8 eV, or 3.2 eV to 2.9 eV, such as 3.17 to 2.95 eV.

Light with photons having "a majority energy in the range from 1.24 eV to 2.48 eV" stands for light, for example in the form of a light beam or light ray, in which at least 50%, in particular at least 60% or at least 70% or at least 80% or at least 90% or at least 95%, of the photons—as indicated by their energy (or wavelength)—have an energy in the range from 1.24 eV to 2.48 eV or 1.3 eV to 2.4 eV, such as 1.4 to 1.6 eV or 1.45 to 1.56 eV.

Generally speaking, it has been found that dosing, in particular simultaneously, dosing of both high and low energy photons, in particular together with a low energy photon activated photosensitizer, increases the antimicrobial effect of light compared to dosing of either group of photons separately. This can be seen in planktonic forms of microbes, but especially in biofilms, when applied as a single dose.

Furthermore, it has been found that this combination, which is also referred to as "dual light treatment", has the capability of sustain the antimicrobial efficacy in a biofilm when the dosing is continued as a daily treatment in long term use.

The treatment using low energy photons together with an exogenous photosensitizer, as practiced in dentistry, tends to lose its efficacy in a biofilm in the long term. There are many reasons for this resistance formation, including activation of genes responsible of influx pump expression. Irrespective of the actual cause, or combination of different explanations, similar phenomena have been encountered when continuing daily dosing of high energy photons in biofilm studies in the context of the present invention.

The improved efficacy of the dual light treatment, as a single dose, and the ability of the treatment to sustain the efficacy, can be explained by simultaneous generation of radical oxygen species by light in the presence of endogenous and exogenous sensitizers. The endogenous sensitizers are photoreactive molecules within the cell. These molecules can be for example proteins containing amino acid side chains or proteins bound to chromophoric prosthetic groups, such as flavins and heme.

In one embodiment, chromophore bound proteins are in key roles of cell function including electron transfer reactions in mitochondria and their oxidation may have deleterious effects.

Damage in the side chain containing proteins may play a significant role in bystander damage. On the other hand, exogenous sensitizers have an ability of achieving rapid and efficient production of radical oxygen species damaging both cell membrane and cell wall structures and when entering the cell, damaging other structures. Targets for reactive oxygen species in biological surface include DNA, RNA, proteins, lipids and sterols.

In a first embodiment, the present technology provides for a method of treating biological surfaces with electromagnetic radiation in the form of light of two different energy levels, a first light with photons having a majority energy in the range from 3.5 eV to 2.8 eV and a second light with photons having a majority energy in the range from 1.24 eV to 2.48 eV. The treatment is carried out by simultaneously directing the photons of the first light and the second light against the biological surface.

As referred to above, generally the term majority energy means that more than 50%, in particular more than 60%, for example more than 70% or more than 80% of the energy of the light lies in the indicated range.

In one embodiment the photons have at least 50% of their energy at 3.17 eV to 2.95 eV and 1.56 eV to 1.45 eV, respectively. In one embodiment, the photons have at least 50% of their energy in a range corresponding to the wavelength of about 390 to 420 nm and 795 to 855 nm, respectively.

In one preferred embodiment, the light employed is non-coherent.

In one embodiment,
non-coherent radiant light energy is generated at least two different energy levels, a first and a second energy level;
from the non-coherent radiant light energy there is provided first light having a wavelength corresponding to the majority energy of the first energy level, and second light having a wavelength corresponding to the majority energy of the second energy level; and
the first and second light is then simultaneously directed against the biological surface.

In one embodiment, the light is generated using an optoelectronic component and device thereof, which is capable of simultaneously emitting a first light consisting of high energy and a second light consisting of low energy photons, said first and said second light amounting to at least 80% of all light emitted from the optoelectronic component or device.

By the light discussed above, endogenous and exogenous excitement of the biological material of the surface is achieved, preferably so as to generate reactive oxygen singlets or reactive oxygen species or both.

By the treatment, biological contamination of surfaces, such as microbial or viral or fungal contamination of biological tissues can be prevented or combatted. The treatment can be used for cosmetic purposes as well as for antimicrobial and antiviral and antifungal therapy.

The light can be used as such or it can be combined with a photo-sensitive substance (a photosensitizer) for the purpose of photodynamic therapy (PDT). This will be discussed in more detail below.

In one embodiment, the high energy photons and low energy photons are applied in conjugation with at least one exogeneous photo-sensitizer, which can be activated with the low energy photons.

In one embodiment, a photo-sensitive substance (a photosensitizer) is provided for use in topical treatment of mammal tissues, wherein said sensitizer is applied to a superficial part of the tissue, such as on mammal skin or on a mucous membrane and the part thus treated is subsequently or simultaneously subjected to light at two different wavelengths, viz. to first light having high energy photons with a majority energy between 2.8 eV and 3.5 eV; and a second light having low energy photons with a majority energy between 1.24 eV and 1.65 eV).

In such an embodiment, the high energy photons are being absorbed by endogenous (intracellular) molecules such as porphyrin or riboflavin with photon energy of 2.48 eV or higher to generate reactive oxygen singlets and reactive oxygen. Simultaneously, low energy photons are being absorbed exogenously (extracellular) by the photo-sensitizer resulting in reactive oxygen singlets and reactive oxygen. Both endogenously and exogenously generated reactive oxygen singlets and reactive oxygen species can inactivate, kill or otherwise reduce the levels of micro-organisms, such as bacteria, virus and fungus, in tissue, biofilm, saliva, skin, plaque and teeth surface and mucous membranes.

In one embodiment of invention the high energy photons are being absorbed by intracellular oxidative stress response mechanisms, such as peroxidase enzyme's flavin group, and thus disrupting pathogen treatment adaptation.

In another embodiment, at least one photo-sensitizer is contacted with micro-organisms, such as bacteria, virus and fungus, in a target, such as in tissue, in biofilm, saliva, skin, plaque and on teeth surfaces and mucous membranes, by applying it on the target with a carrier.

Thus, the photo-sensitizer(s) can be applied in the form of an aqueous solution, an alcohol containing solution, a hydrophilic gel, a hydrophobic gel, a hydrophilic polymer, a hydrophobic polymer or in the form of a paste, lotion, tablet, tape, plaster or band-aid.

It would appear that high energy photons and low energy photons penetrate to different depths into micro-organisms or into tissue, biofilm, saliva, skin, plaque and teeth surface and mucous membranes. Thus, by the present technology reactive oxygen singlets and reactive oxygen species are generated at different depths in targets, such as in tissues, biofilms, saliva, skin, plaque, teeth surface and mucous membranes, thus inactivating, killing or otherwise destructing, or at least reducing the content of, micro-organisms, such as bacteria, virus and fungus.

As will be shown in the examples with particular reference to one species of gram positive bacteria (*Streptococcus mutans*), the present technology is effective against bacteria. Thus, generally, gram positive bacteria are represented by the genera *Streptococcus*, e.g. *Streptococcus pyogenes, Streptococcus agalactiae, Streptococcus dysgalactiae, Streptococcus bovis, Streptococcus anginosus, Streptococcus sanguinis, Streptococcus suis, Streptococcus mitis*, and *Streptococcus pneumoniae, Staphylococcus*, e.g. *Staphylococcus aureus, Staphylococcus epidermidis, Staphylococcus simulans, Corynebacterium, Listeria, Bacillus, Clostridium, Rathybacter, Leifsonia*, and *Clavibacter.*

One further group of bacteria to be targeted by the present technology is represented by gram negative bacteria, such as bacteria of the phyla *Proteobacteria, Aquificae, Chlamydiae, Bacteroidetes, Chlorobi, Cyanobacteria, Fibrobacteres, Verrucomicrobia, Planctomycetes, Spirochetes, Acidobacte-* ria, *Actinobacteria, Firmicutes, Thermotogae, Porphyromonas* and *Chloroflexi*. Specific examples include the following: *Escherichia coli, Salmonella*, such as *Salmonella enteritidis, Salmonella typhi, Shigella, Pseudomonas, Moraxella, Helicobacter, Stenotrophomonas, Bdellovibrio, Neisseria gonorrhoeae, Neisseria meningitidis, Moraxella catarrhalis, Haemophilus influenza, Klebsiella pneumoniae, Legionella pneumophila, Pseudomonas aeruginosa, Escherichia coli, Proteus mirabilis, Enterobacter cloacae, Serratia marcescens, Helicobacter pylori, Porphyromonas gingivalis, Aggregatibacter actinomycetemcomitans* and bacteria of the genus *Acinetobacter*, for example *Acinetobacter baumannii, Acinetobacter albensis* and *Acinetobacter apis*.

The treatment is also effective against viruses, such as Adenoviruses, Herpesviruses, Poxviruses, Parvoviruses, Reoviruses, Picornaviruses, Togaviruses, Orthomyxoviruses, Rhabdoviruses, Retroviruses, Papillomavirus and Hepadnaviruses.

Treatment has also shown effectivity against fungus such as *Candida* species in particular *Candida albicans*.

As discussed below in detail, the photo-sensitizer can be mixed with a carrier to provide the photo-sensitizer in the form of a solution, gel, paste, lotion or even plaster, tape, tablet or band-aid capable of application on the biofilm or infected area of target tissue or other biological surface. Typically, the photo-sensitizer is present in the composition (such as solution, gel, paste, lotion, plaster, tape, table or band-aid) at a concentration of 0.001 to 1% by weight, in particular 0.004 to 0.5% by weight.

The photo-sensitizer is typically applied, for example in liquid form as a gel, in amounts of about 0.01 mg/ml to 10 g/ml, for example 0.1 mg/ml to 1 g/ml.

In some embodiments, the photo-sensitizer is applied typically onto the target area, such as tissue, biofilm, saliva, skin or plaque, at 0.0001% (w/v) to 1% (w/v).

In one embodiment, a method according to any of the above embodiments is carried out using an anti-microbial optoelectronic component and device thereof, such as an LED light source, by simultaneously emitting high energy photons absorbed by endogenous molecules and low energy photons absorbed by exogenous molecules.

In a further embodiment, the anti-microbial optoelectronic component and device thereof, used in a method according to any of the above embodiments, is emitting high energy and low energy photons and feed-in voltage or current is alternated or pulsed at a frequency of 1 Hz to 1 GHz, for example 1 to 100 MHz, independently from each other.

In a further embodiment, the anti-microbial optoelectronic component and device thereof, used in a method according to any of the above embodiments, is simultaneously emitting high energy (in the range of 2.48 eV and 1.24 eV) photons and low energy photons (in the range of 3.5 eV and 2.8 eV). According to this embodiment the optoelectronic device may comprise an optional photo detector to detect photo luminescence of the endogenous and exogenous molecules or their photo decomposition side products.

An embodiment comprises an optoelectronic component and device thereof having a plurality of semiconductor chips that are connect in series or in parallel, the chips exhibiting emission energy that can be varied in the range of 2.48 eV and 1.24 eV and in the range of 3.5 eV and 2.8 eV, respectively.

In embodiments, the optoelectronic components or devices referred to in the fore-going two paragraphs, can also be capable of emitting energy at 1.3 eV to 2.4 eV, such as 1.4 to 1.6 eV or 1.45 to 1.56 eV; and at 3.2 eV to 2.9 eV, such as 3.17 to 2.95 eV, respectively. The area of the target to be treated can vary. In one embodiment, the area is about 0.1 $cm^2$ to 4 $cm^2$. Such a limited treatment area is typical for topical treatment, for example for treating parts of a mammal's skin or other areas exhibiting infection or biofilm or both. In another embodiment, the treatment area is about 10 to 100 $cm^2$. This area applies to situations of tooth treatment, which can be reached by using a mouth piece.

The power or wattage to be directed towards the target area varies typically in the range of 0.01 W to 500 W, in particular about 0.1 to 50 W, for example 1 to 25 W.

The dosage varies from about 0.1 to 1000 $J/cm^2$, in particular from 1 to 500 $J/cm^2$, for example from 1 to 250 $J/cm^2$ or 1.5 to 120 $J/cm^2$ or 2.5 to 75 $J/cm^2$.

In one embodiment, light is directed to the target area at 0.001 $W/cm^2$ to 2 $kW/cm^2$, preferably 0.01 $W/cm^2$ to 20 $W/cm^2$, in particular about 0.050 $W/cm^2$ to about 10 $W/cm^2$, for example about 0.075 $W/cm^2$ to about 5 $W/cm^2$, such as 0.1 $W/cm^2$ to about 2.5 $W/cm^2$. This can also be referred to as power density of the light.

The treatment time can vary. Typically, the duration is from 0.5 s to 120 min, in particular 0.5 s to 10 min, for example 0.5 s to 300 s or 1 s to 180 s.

As a result of the treatment, there is typically a temperature increase in the target area. In one embodiment, the temperature increase varies in the range of about 0.1 to 20° C., for example 0.2 to 10° C. and in particular about 0.5 to 5° C. The localized peak temperature in specific treatment site can exceed before mentioned values for limited time (typically less than 30 sec, in particular less than 15 sec).

In one embodiment, the treatment is carried out by using light, in particular non-coherent light, at a first wavelength from 400 to 430 nm (corresponding to photons of about 3.1 eV to 2.9 eV), preferably at a dosage of 1 to 120 $J/cm^2$, and in particular with a power density of from about 10 to about 2500 $mW/cm^2$ for a period of time from 0.5 s to 120 min, and at a second wavelength from 780 to 830 nm (corresponding to photons of about 1.59 eV to 1.49 eV), preferably at a dosage of 1 to 120 $J/cm^2$, and in particular with a power density of from about 10 to about 2500 $mW/cm^2$ for a period of time from 0.5 s to 120 min.

In an embodiment according to the invention an optoelectronic device is used in a method of producing and delivering photodynamic radiant energy for preventing or for therapeutically treating diseases comprising the steps of
  (i) generating a non-coherent radiant light energy at multiple energy levels;
  (ii) providing a media or molecules capable of absorbing at least a part of the radiant energy;
  (iii) delivering light energy in substantially exact light energy wavelength needed to photoactivate the media or molecules capable of absorbing at least a part of the radiant energy; a preventing or therapeutic disease treatment; and
  (iv) preventing or therapeutically treating a target by endogenously, exogenously or both endogenously and exogenously generating reactive oxygen singlets and reactive oxygen species in said target.

One embodiment of the invention is that the optoelectronic device is used for programmed cell death of pathogenic micro-organisms, such as bacteria, virus or fungus, controlled by combination of high and low high photons and endogenous photosensitive compound or multiple different of compounds.

As mentioned above, in one embodiment, the light treatment of any of the above embodiment is carried out by way of photodynamic therapy (PDT). Such therapy comprises light and non-toxic target molecule that is activated by light. The target molecule absorbs a photon's energy and achieves an excited state. The target molecule can then exit this state by emission of a photon (fluorescence light), emission of heat or forming so called triplet state. This triplet state can then react with oxygen through charge transfer (type I reaction) or by transferring energy (type II reaction). In type I mechanism, charge is transferred to a substrate or to molecular oxygen generating reactive oxygen species like hydrogen peroxide and oxygen radicals like superoxide ions or free hydroxyl radicals. In type II mechanism, energy only—not charge—is transferred directly to molecular oxygen, whereby the highly reactive singlet oxygen ($^1O_2$) originates.

The antimicrobial effect of PDT is based on an oxidative burst upon illumination and relies on damage to cellular structures and molecules, therefore being an unspecific mechanism. This burst is immensely reactive and thus having short below 0.3 micrometers effective range thus making the treatment location specific.

The ratio between different action mechanism and the activation wavelengths is target molecule specific thus PDT, PTT and PHT treatment must be engineered specifically for certain light and target molecule compositions. Some photosensitizers or target molecules have higher ability to generate heat and others react through triplet state formation. For example, Indocyanine green (ICG) releases over 80% of absorbed energy as heat but porphyrins have singlet oxygen quantum yield between 0.5 to 0.8. Thus, selection of photosensitizer(s) will also define the classification of the treatment to photodynamic, photothermal or photo hyperthermia as the exact mechanism of pathogen killing can vary.

The photothermal effect is related to local heating of the pathogen. One possible approach of pathogen killing is to use pathogen selective heat generating photosensitizer with proper wavelength to locally heat the target pathogens. Biofilms have a lower cooling capability than healthy tissue as they lack active blood circulation and thermal conductivity.

In addition to exogenous photosensitizer activation the administered photons can affect pathogens through interactions with pathogen endogenous molecules. Flavin and porphyrin photoreaction in crucial in blue light induced intrinsic mechanism to kill the bacteria.

There are several bacterial counterparts to plant phototropins, the blue-light sensing flavin binding proteins and/or iron-free porphyrins. Three major classes of flavin photosensors in bacteria, LOV (Light, Oxygen, Voltage) domains, BLUF proteins (Blue Light sensing Using flavin adenine dinucleotide, FAD) and cryptochromes regulate diverse biological activities in response to blue-light.

The bacterial LOV-proteins exhibit a variety of effector domains associated to the light-responsive LOV-domain, e.g. histidine kinase, transcriptional regulators, putative phosphodiesterase's and regulators of stress factors, pointing to their physiological role as sensing and signaling proteins. Thus, the application of certain energy photons might alter the bacterial response to the given therapy. A considerably large number of the bacterial LOV proteins are members of the histidine protein kinase superfamily. Histidine kinases are multifunctional, and in bacteria typically transmembrane proteins of the transferase class of enzymes that play a role in signal transduction across the cellular membrane. For example, bacterial influx pumps, responsible in drug resistance can be histidine kinases.

Histidine kinase receptor activation can be located in periplasmic-sensing, transmembrane-sensing or cytoplasmic-sensing.

BLUF proteins can control the expression of genes related to photosynthesis through a light-sensitive proteins, which interact with a DNA-binding protein. Many BLUF proteins carry an extra domain downstream from the BLUF domain, with enzymatic or other properties, and the majority of these proteins appear to be homodimers. A protein called BlrP1, for example, is a dimeric cyclic nucleotide phosphodiesterase from Klebsiella pneumonia that shows a fourfold increase in enzyme activity under light conditions. AppA and PAC are just two examples of many photosensitive proteins carrying the BLUF domain, about 100 amino acid residues long, that is responsible for the detection of light, these are called "group 1" proteins. Many other BLUF proteins have fewer than 200 amino acid residues and are designated "group II" proteins. These proteins have little more than the BLUF domain in each subunit, but may carry secondary structural elements in the C-terminal region that are required for stability.

Photolyases and cryptochrome blue-light photoreceptors are evolutionarily related flavoproteins that perform distinct functions. Photolyases repair UV-damaged DNA in many species in bacteria similar to cryptochromes.

In antiviral treatment the viral population is targeted simultaneously with three or more antiviral drugs.

In antifungal treatment, the fungal population is targeted simultaneously with one, two, three or more antifungal drugs.

As described above in one embodiment, a treatment is carried out that combines exogenous effect to sites of administered benefit agent(s) that can consist of cell wall structures, EPS matrix, cell to cell signaling and endogenous effect where pathogen internal molecules are affected in their functional surroundings.

This treatment targets key functional sites and outer and internal membrane structures creating oxidative burst that is difficult to control by bacteria oxidative stress response mechanisms and temperature stress to further destabilize cell wall and cytoplasmic membrane. Described wide scale attack goes far beyond traditional PDT as the pathogen & pathogen population is attacked in different sites with oxidative and temperature burst exogenously and endogenously.

PDT, PHT and PTT can be potentiated also by adding active molecules or disinfectant compounds that breach cell wall structures, disinfectants capable of altering cell wall stability, external heating of target area, use of singlet oxygen scavenger that can act as reactive oxygen transporters, use of ion scavengers that removes divalent ions and thus destabilizes bacteria cell wall of gram negative bacteria, use of ion pump inhibitors to increase endogenous concentration of photosensitizer, applying immune response stimulators, microbial efflux pump inhibitors, protein transport e.g. porins stimulators, and topic use of antibiotic or antibacterial substances as photosensitizers or in conjunction with the photosensitizer.

One embodiment comprises using during a first period of time a first photosensitizer and during a second period of time a second photosensitizer, which is different from the first photosensitizer. Typically, the first photosensitizer and the second photosensitizer can be activated using first light and second light, respectively. Preferably, first and second photosensitizers are used in combination, or alternatingly or at least one of them is used at a predetermined point of time during the treatment.

In one embodiment, the first photosensitizers are selected from the group comprising high energy photon activated photosensitizers ("type-I photosensitizers"), whereas the second photosensitizers are selected from the group comprising low energy photon activated photosensitizers ("type-II photosensitizers").

One potential approach to treatment is to adjust the treatment ratio of type I and type II mechanisms based on observed efficacy during treatment. Treatment can combine I and II mechanism at same time or rely more on one of the mechanisms and add/replace the compound working through the other mechanism in specific intervals to further increase the treatment efficacy.

For example, combining type-II photosensitizer with low energy photons and high energy photons with episodic addition of type-I photosensitizer or a pigment that generates reactive oxygen through charge transfer processes. One possible combination is to combine type II photosensitizer indocyanine green with type I photosensitizer curcumin with high and low energy photons. Treatment can also be monitored and the mechanism to be changed when a specific event is detected.

In one embodiment, treatment potentiation is achieved by pulsing the light to allow replenishment of target molecules, such as oxygen, during the dark periods, or by adding extra target molecules to treatment, such as super oxygenated water or oxygen generating compounds, such as peroxo compounds, for example hydrogen peroxide. This embodiment in particular aims at increasing the amounts oxygen present to enhance the effect of the photodynamic therapy.

The wait time between pulses can be 0.01 to 100 times the length of the treatment pulse. This is particularly important as the maximum treatment power is limited by heat generation and heat dissipation. Treatment is more effective and the time needed for treatment shorter if the light is delivered in a way that allows generation of active oxygen.

Typically, the treatment pulse time is in the range of 0.01 to 120 s, in particular 0.5 to 60 s, for example 0.5 to 30 s.

Use of high and low energy photons is beneficial as the different energy photons have different tissue stimulating properties. Low energy photons can have beneficial tissue heating of 2.7 degrees to a depth of 2 cm. This increases oxygen partial pressure and blood circulation that subsequently stimulates the metabolism of the cells including the promoted immune reaction.

High energy photons, particularly photons with energy of 3.06 eV, have endogenous bacteria killing effects but the penetration of this wavelength to tissue is limited. These same target molecules can be activated through a photon up-conversion reaction where two or more photons absorb simultaneously to excite the target molecule to a higher energy state.

In one embodiment, the selection of 3.06 eV and 1.53 eV is a particularly good combination. 1.53 eV (corresponding to a wave length of 810 nm) has exactly ½ of the photon energy of that of 3.06 eV (corresponding to a wave length of 405 nm) but it has much higher tissue penetration. Thus, by subjecting the target to simultaneous absorption of 1.53 eV photons and 3.06 eV photons, can excite endogenous porphyrins creating antibacterial effect in addition to tissue healing effect. High energy photons reduce the formation of biofilm extracellular polysaccharides matrix which synergies with exogenous PDT and reduces pathogenicity of biofilms.

The invention is suitable in treatment of conditions caused by pathogens, like bacteria, virus and/or fungus, on skin, in the mouth, on the surface of teeth, gums, mucosal membranes, throat and genitals.

The method can also be carried out such that light only is used for tissue stimulating purposes.

The PDT treatment is nonspecific and thus generating resistance against it is inherently difficult. The robustness of PDT treatment can be increased by using different types of photosensitizers that work through singlet oxygen, charge transfer as well as heat generation. The aspect of heat induced pathogen killing, photothermal therapy, is fundamentally even more robust than PDT. These two techniques have synergistic effect which makes combination of these highly effective system.

Even as the treatment is highly robust the selectivity of more treatment withstanding bacteria species will happen. In oral setting this can be mitigated by focusing treatment to area of interest and leaving other areas untreated. This will keep changes to mouth flora minimal compared to antibacterial mouthwashes and provide efficient bacterial killing in the site of interest, for example surfaces of teeth and gums.

Light system can also include tissue stimulating light such as near infrared that has deep penetration into tissue and which is known to stimulate blood circulation and immune response.

Light can also be used to stimulate teeth bone formation and device heat can be used to increase the fluoride binding to enamel in addition of potentiating PDT and PTT treatment.

Device has important function as heat generating surface that increases the treatment effect and increases the fluoride binding rate it also helps the fluoride and photosensitizer to penetrate deeper into biofilm through thermal diffusion. This further increases the treatment effectivity.

The biofilm metabolism and bacteria composition changes when biofilm ages from 0 hours to mature biofilm of 96 hours old. This sets pressure to PDT treatment as different ages of biofilm 0, 12 h, 24 h, 32 h, 48 h, 72 h and 96 h require different treatment for most efficient overall treatment outcome.

The photosensitizer can be highly specific for biofilm, making its inherent optical and light properties (reflection, absorption, fluorescence, transmission, bleaching) a mean to detect and measure bacteria biofilm properties such as coverage and thickness. The absorbed light will also heat the target tissue thus making possible to measure tissue health by comparing temperature difference in different tissue locations. In particular by heat monitoring it's possible to detect cancer tissue or inflammation, as they have lower cooling capability compared to healthy tissue. Absorption and time dependent bleaching and fluorescence intensity can be used to measure the biofilm thickness and bacteria amount thus making possible better follow disease state or overall health of the target area. Monitoring is particularly useful to monitor chronic periodontitis and gum health, and in early detection of cancers.

For treatment monitoring purposes and for safety of continuous treatment the photosensitizer can have selectivity to target tissue resulting in higher light absorption in target biofilm compared to clean dentin or healthy tissue when monitored with fluorescence microscope set to monitor the absorption maximum of the photosensitizer. Monitoring data can be used to adjust treatment to adapt changes during treatment, such as bleaching of one or more photosensitizers or direction of power to high biofilm areas or plan a personalized treatment options such as more frequent use, guide to focus mechanical cleaning to certain area or recommend an expert visit.

Mineralization process can be monitored with different light absorption and emission of sites going through remineralization and sites where enamel is disappearing. Particularly use of blue light together with NIR light allows simultaneous detection of deeper cavities as well as surface changes of the tooth and enamel.

Indocyanine green goes through red shift upon binding to pathogens, it is possible to quantify and characterize biofilm and its total amount by measuring red shift and the rate of photobleaching. The total absorption and rate of photobleaching corresponds to thickness of biofilm and to amount of active substance in the biofilm. Furthermore, spectrometer analysis can be used to detect plaque properties, such as sugar levels, pH-levels, fats, calorie content, protein content, amount of extracellular polymetric substance in biofilm. For these purposes the optoelectronic device used in treatment can incorporate micro-spectrometer sensors, temperature sensors, light sensors, pH sensors, force sensors, gyroscopes, pressure sensors.

Two or more photons can absorb simultaneously to give rise to super excited state that have distinct fluorescence and chemical properties. The energy of super excited state is higher than the normal excitation state. The rate of super excited state formation can be used quantify biofilm thickness and detect pathogens deeper in the tissue.

As described before the treatment effect can be potentiated by inhibition of microbial efflux pumps, affecting biofilm external and internal EPS matrix, affecting outer structures of pathogen, through disruption of pathogen to pathogen communication or quorum sensing, providing higher concentration or oxygen or reactive oxygen to target site, stimulating immune response, promoting oxidative stress transfer, use of enzymes, increasing active substance uptake into pathogen and biofilm, addition of chemical quenchers of singlet oxygen (carotenoids, Beta-carotene, and alpha-tocopherol)

Addition of inorganic salts, particularly potassium iodide, addition of divalent ions, disinfectants, carrier liquid and topic antibiotics is possible. Photons can be used to activate and potentiate effect of topic antibiotics as well as together with such antibiotic treatment to reduce or prevent bacteria antibiotic resistance formation and to stimulate tissue healing and immune response.

Treatment can be combined with topic use of antibiotics and disinfectants for synergist antipathogen effect. For example, the use phototherapy with chlorhexidine to target biofilms is new to oral disinfection. The results of dual wavelength photodynamic therapy with chlorhexidine against *Streptococcus mutans* biofilm shown in appendix III are completely new. The use of high and low energy photons with photosensitizer increased substantially the antibacterial effect against biofilm and thus provides promising new approach for improvement biofilm treatment. The effectivity is based on photon and anionic photosensitizer ability to penetrate deeper into biofilm and provide efficient bacteria killing inside the biofilm as well as on the surface. The chlorhexidine effect is mostly present only on the surface of the biofilm. High energy photons reduce the biofilm EPS matrix formation that further increases the chlorhexidine effectivity in subsequent treatments.

Possible application methods of active ingredient to target site consist of aqueous solution, alcohol containing solution, chlorhexidine containing solution, hydrophilic gel, hydrophobic gel, hydrophilic polymer, hydrophobic polymer, paste, lotion, tape, plaster or band-aid.

Aqueous solutions of the above kind include mouth rinses. In particular, photosensitizer is used with a chlorhexidine solution or mouth wash.

In an embodiment, the benefit agent is delivered with a device that can be a film of 1 nm to 10 mm thick, gel, emulsion which can consist of polymers, inorganic molecular networks, nano/micro particles/fiber assemblies, fiber networks, nonwovens, foams, hydrogels, paste or combinations of these components.

The substrate with benefit agent can be attached, placed on top or inside or to be separate from the optoelectronic device applying the light.

In one embodiment, benefit agents like ICG are kept in hydrophobic or amphiphilic medium for better stability in storage and easy administering. This can be achieved by incorporating benefit substance in film or gel or into hydrophobic or amphipathic carrier liquid or gel. On of such application is a gel what has DMSO as main solvent. Dry gel consists of hydrophobic substance that has gel like characteristics for example gel where one ingredient is polydimethylsiloxane (PDSM). The gel can be categorized as slow drug release gel and active substance can be incorporated into gel independently or together with molecules categorized as antibiotics.

Film, gel or emulsion consisting of organic or inorganic polymer that has photosensitizer and possibly one or more potentiating compounds embedded. Film, gel and emulsion can have capillary function thus allowing water to enter when placed on moist surface. Film, gel and emulsion is transparent to treatment light. Film, gel or emulsion can consist of polymer that can be left on the treatment surface for subsequent treatment and for protection of site from other pathogens and dirt. Particular use of film, gel or emulsion is in treatment of aphthous stomatitis lesions, herpes sores and skin wounds.

Thin film, gel or emulsion can be partly or fully made to be water soluble wherein the water-soluble polymer is pullulan, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, Arabic gum, polyacrylic acid, methylmethacrylate copolymer, carboxyvinyl polymer, amylase, high amylase starch, hydroxypropylated high amylase starch, dextrin, pectin, chitin, chitosan, levan, elsinan, collagen, gelatin, zein, gluten, soy protein isolate, whey protein isolate, or casein.

Two light sources can be manufactured into same LED casing or incorporated into single light emitting surface. The emitted amount of between high energy photons and low energy photos can be from 50%-50% distribution to 1%-99% or vice versa 99%-1% or in between. Having low and high energy photons together contributes to more eye safe solution as the photons act through different mechanisms have different optical properties and total needed intensity is lower than only having high or low energy photons.

The ratio between high energy photons and low energy photons can be adjusted to target biofilms of different age and different bacteria species.

In one embodiment, the ratio between the emitted amount of high energy photons and low energy photons is 0.2:1 to 5:1, in particular 1:1 to 3:1.

In one embodiment, the present light sources or optoelectronic device are capable of providing dualwave therapy where high energy photons are used to stimulate bacteria gene expression to increase treatment efficacy long term.

Based on the above, a first embodiment provides for an optoelectronic device capable of emitting high energy photons with majority energy between 2.8 eV and 3.5 eV and low energy photons with majority energy between 1.24 eV and 1.65 eV, with or without a photosensitizer, enabling a method for sustained antimicrobial effect in preventive and curative dental/oral care for long term use.

A second embodiment provides for an optoelectronic device of the afore-mentioned kind, where two wavelengths are emitted simultaneously or at a time interval of 0.001 to 1000 ms, for example 100 ms, from each other.

An optoelectronic device may comprise a light emitting component that has two or more light emitting surfaces (EPIs).

An optoelectronic device may also comprise has sensor capable of monitoring treatment progression, plaque amount. It is preferred that the optoelectronic device is capable of adjusting the treatment light based on the monitor feedback.

Different designs for optoelectronic devices are possible. The device can have tooth brush type shape, it can be a mouth piece or a rod like illuminator. The optoelectronic device used in treatment can incorporate micro-spectrometer sensors, temperature sensors, light sensors, pH sensors, force sensors, gyroscopes, and pressure sensors.

Based on the above, the present technology also provides a kit for treatment of microbial, viral or fungal infections of tissue, in biofilm, saliva, skin, plaque, on teeth surfaces and in mucous membranes.

In one embodiment, the kit comprises at least two components, viz. an optoelectronic component or device thereof and at least one photosensitizer. The optoelectronic component or device is capable of simultaneously emitting a first light consisting of high energy and a second light consisting of low energy photons. Typically, said first and said second light amount to at least 80% of all light emitted from the optoelectronic component or device. The photosensitizer is of a kind which can be activated by at least either of the high energy and low energy photons. It is possible also to employ photosensitizers that can be activated by both of the high energy and low energy photons. The photosensitizer can be of any of the above mentioned kinds.

In a second embodiment, the kit comprises an optoelectronic device capable of emitting high energy photons with majority energy between 2.8 eV and 3.5 eV and low energy photons with majority energy between 1.24 eV and 1.65 eV, together with a photosensitizer or a plurality of photosensitizers, capable of carrying out a method for achieving a sustained antimicrobial effect in preventive and curative dental/oral care for long term use.

A third embodiment provides for a kit comprising an optoelectronic device, in particular of the kind disclosed in the fore-going, and wherein two wavelengths are emitted simultaneously or with a time interval, such as a time interval of 0.001 ms to 10 s, or 0.001 ms to 1000 ms, for example 10 to 500 ms or about 100 ms, from each other, optionally together with a photosensitizer or a plurality of photosensitizers, capable of carrying out a method for achieving a sustained antimicrobial effect in preventive and curative dental/oral care for long term use.

In one alternative, one LED or several LEDs are pulsed with a high frequency, such as 1 to 50 MHz, for example about 10 MHz, to achieve high and low energy photons.

A fourth embodiment provides for a kit comprising an optoelectronic device having a light emitting component that has two or more light emitting surfaces (EPIs), optionally together with a photosensitizer or a plurality of photosensitizers, capable of carrying out a method for achieving a sustained antimicrobial effect in preventive and curative dental/oral care for long term use.

A fifth embodiment provides for a kit comprising an optoelectronic device according to any of the fore-going embodiments, further comprising a sensor capable of monitoring treatment progression. In particular, the kin comprises an optoelectronic device comprising a sensor capable of detecting treatment progression and of producing a regulation signal based on the progress of the treatment, said sensor being coupled to the optoelectronic device do adjust the light emitted from the optoelectronic device depending on the regulation signal.

A sixth embodiment provides a kit comprising an optoelectronic device further exhibiting the shape of a tooth brush, or the shape of a mouth piece which can be inserted in a mouth between the biting surfaces of the teeth, or the shape of a rod like illuminator.

The optoelectronic device used in any kit or treatment can incorporate micro-spectrometer sensors, temperature sensors, light sensors, pH sensors, force sensors, gyroscopes, and pressure sensors.

In the embodiments disclosed above, the optoelectronic device preferably comprises a semiconductor light source, in particular it comprises light-emitting diodes (LED) as a light source. In embodiments, the light-emitting diode(s) can have one or several light-emitting surfaces. An LED light source will be capable of achieving the PDT without damaging the treated area. The dosage and power of the light emitted from the LED can be varied by adjusting the power input from an external power supply.

In a preferred embodiment, the optoelectronic device, in particular LED device, is capable of emitting non-coherent light at a first wavelength from 400 to 430 nm (corresponding to photons of about 3.1 eV to 2.9 eV), preferably at a dosage of 1 to 120 J/cm$^2$, and in particular with a power density of from about 10 to about 2500 mW/cm$^2$ for a period of time from 0.5 s to 120 min, and at a second wavelength from 780 to 830 nm (corresponding to photons of about 1.59 eV to 1.49 eV), preferably at a dosage of 1 to 120 J/cm$^2$, and in particular with a power density of from about 10 to about 2500 mW/cm$^2$ for a period of time from 0.5 s to 120 min.

It should be pointed out that in any of the above embodiments, the targeted photosensitizer or the photosensitizer that is subjected to the high or low energy photons, or both, can be one or several inherent molecules capable of photodynamic reaction upon light excitation.

The following represent further embodiments:

A kit where a where device is capable of detecting treatment progression and state through radiation sensitive sensor or sensors. For example detect change in Indocyanine green optical properties, change in temperature or bleaching of indocyanine green.

A kit where a tooth whitening substance is used with dual wavelength light source or together with photosensitizer A kit consisting of active substance in easily applicable form and light applicator capable of dual light activation.

A kit comprising of photosensitizer in form of water soluble effervescent tablet and hand held light applicator capable of emitting dual light photons.

A kit comprising of photosensitizer in the form of a water soluble effervescent tablet, gel, or paste, a one-time use mouth piece and light applicator.

The photosensitizer of the kit can for example be provided in the form of photosensitizers incorporated or inherently present in berry extracted mouth rinse.

The kit may also include hydrogen peroxide as potentiating compound.

Further, based on the afore-mentioned, the following represent preferred embodiments:

1. A composition comprising a photo-sensitive compound and a media, said media comprising:
    (i) an aqueous phase;
    (ii) high energy photons with majority energy between 2.8 eV and 3.5 eV; and
    (iii) low energy photons with majority energy between 1.24 eV and 1.65 eV.
2. A composition comprising a photo-sensitive compound and a media, said media comprising:
    (i) a PDMS gel;
    (ii) a biofilm;
    (iii) high energy photons with majority energy between 2.8 eV and 3.5 eV; and
    (iv) low energy photons with majority energy between 1.24 eV and 1.65 eV.
3. The composition of embodiment 1 or 2, wherein said photo-sensitive compound is selected from the group consisting of photon absorption at the energy range of 1.24 eV and 1.65 eV.
4. The composition of any of embodiments 1 to 3, wherein the photo-sensitive compound is indocyanine green.
5. The composition of any of embodiments 1 to 4, wherein the photons have at least 50% of energy in 3.17 eV and 2.95 eV and 1.56 eV and 1.45 eV.

Experimental

In a first series of tests, dye plaque specificity was observed in room light after treatment with hamamatsu 1394 and NIR light source.

Figure 2:
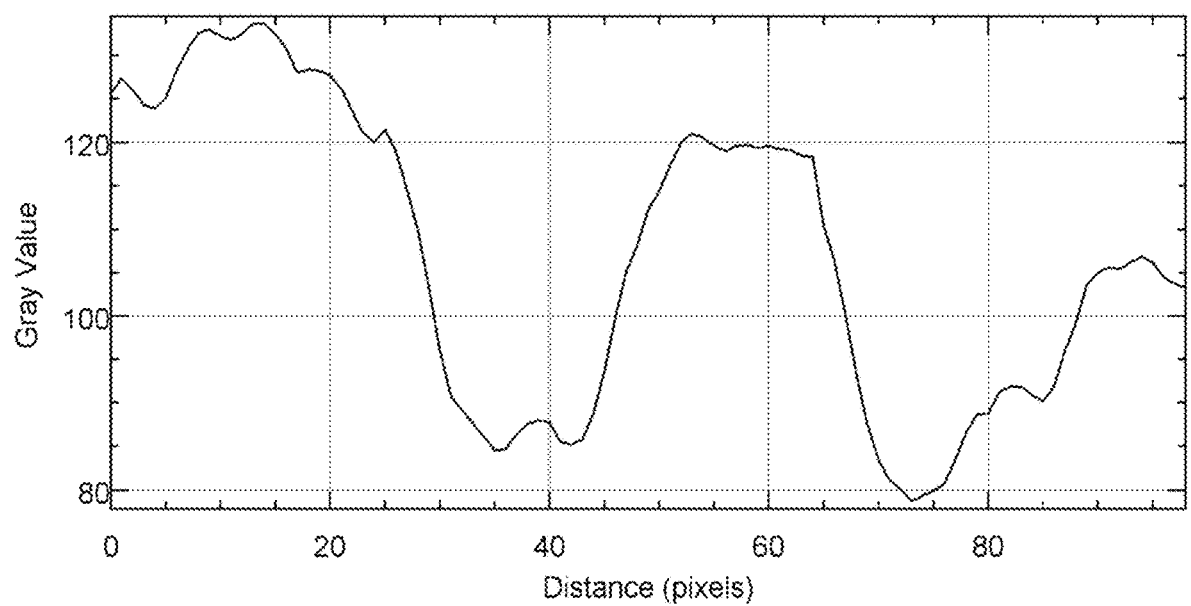
FIG. 2 is a diagrammatic depiction of gray level fluctuation to indicate dye light absorption.

As seen in FIGS. 1 and 2, respectively, there is distinct intensity difference between non-biofilm areas of the teeth and gums and the areas where biofilm is present. Treatment is focused on the biofilm areas which are represented as dark in the FIG. 1 and with lower grey value in FIG. 2.

Figure 3:
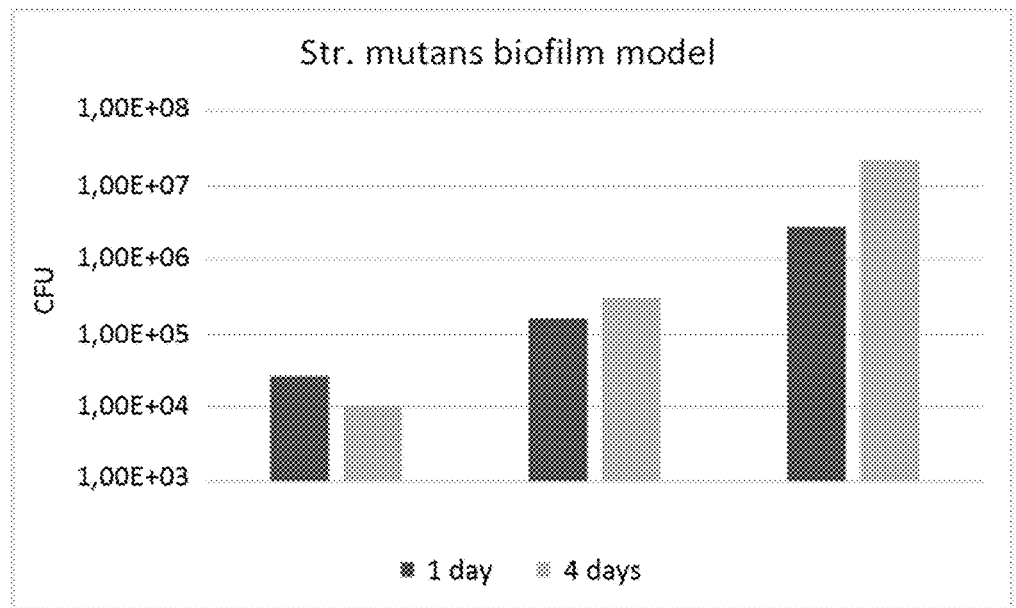
FIG. 3 is a bar chart showing the antimicrobial effect of chlorhexidine potentiated with dual wavelength PDT according to an embodiment of the invention.
Figure 4:
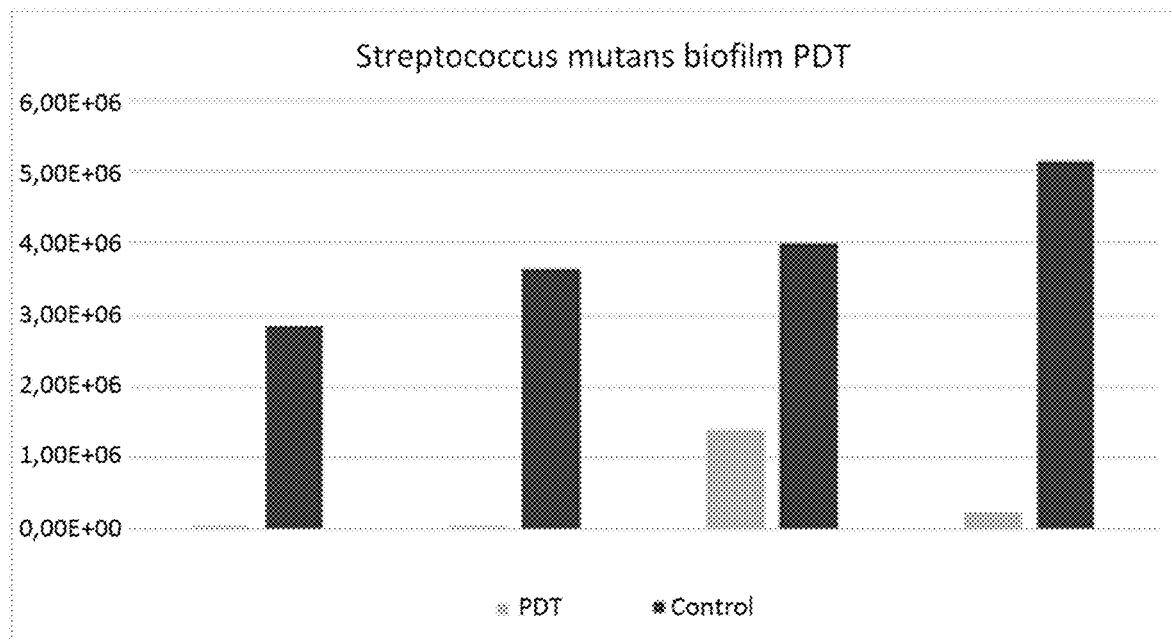
FIG. 4 is a bar chart showing the antimicrobial effect of PDT treatment on 1, 2 and 4 days old *Streptococcus mutans* biofilms.
Figure 5:
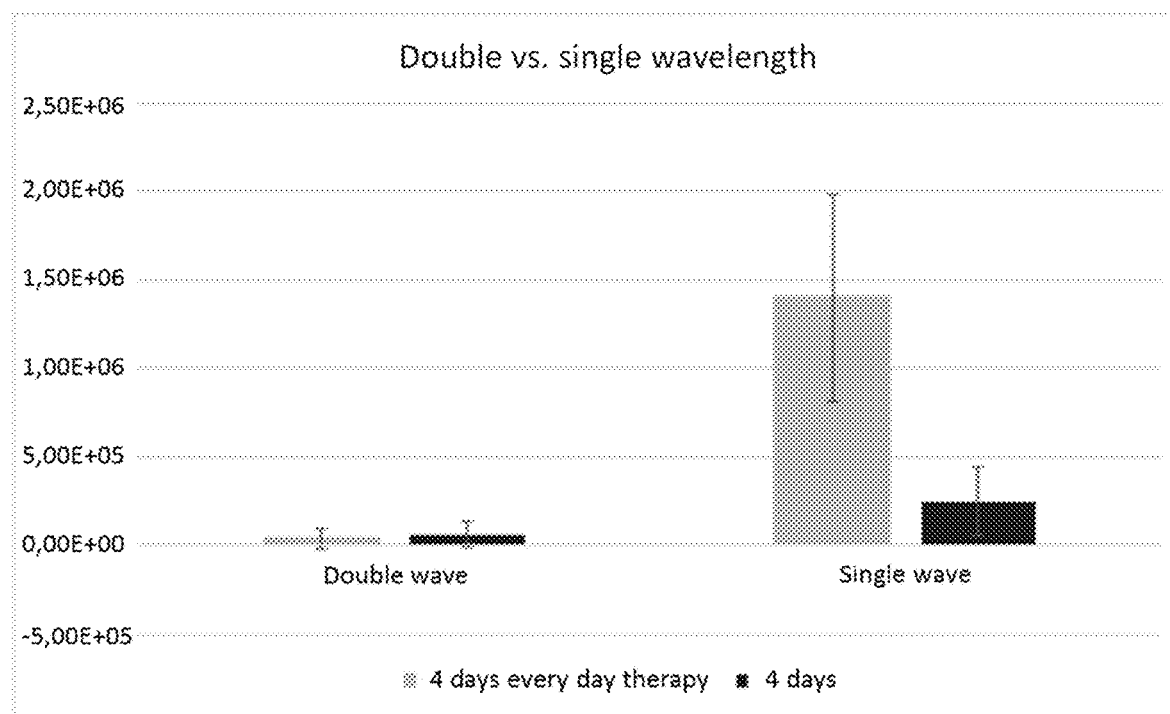
FIG. 5 is a bar chart showing the efficiency of double wavelength and single wavelength treatments on 4 days old biofilms.

In a second series of tests, potentiation of chlorhexidine with dual wavelength PDT was evaluated. The results are shows in FIG. 3 which indicates that the a combination of multi wavelength PDT with chlorhexidine gives a much stronger effect than reference and treatment with only one wavelength.

In a third series of test, the adaptability of *Streptococcus mutans* biofilms to multi and single wavelength PDT treatments, respectively, was compared.

Two separate monospecies biofilm model experiments were performed to study the effect of reoccurring photodynamic therapy on biofilm formation. The *Streptococcus mutans* biofilm experiments were divided in different classes based on biofilm age and the therapy given.

The one-time PDT treatment was performed for 1 day, 2 days and 4 days old biofilms. This effect was then compared to every day treated 4 days old biofilms with the hypothesis that the biofilm growth would be strongly suppressed in the everyday treated sample. The viability of the bacteria was assessed by serial dilution CFU method which was performed after the last photodynamic therapy treatment.

Materials and Methods

*Streptococcus mutans* (ATCC 25175) bacteria was grown over 18 h in growth chamber (36° C., 5% $CO_2$) in BHI-broth (Bio-Rad 3564014). The resulting bacteria suspension was diluted with 0.9% NaCl suspension to optical density of 0.46.

Biofilm was grown on bottom of well plate by adding 100 µl diluted *Streptococcus mutans* suspension in each well with 100 µl of BHI-broth growth medium. The bacteria plate was incubated in growth chamber (36 Celsius, 5% $CO_2$) and BHI-broth medium changed daily.

Exposure:

Before the light exposure, the growth medium was replaced with indocyanine green suspension which was let to incubate in dark in room temperature for 10 minutes. After the incubation the biofilm was washed twice with 0.9% NaCl solution. The treatment time was calculated from desired light amount and known intensity.

The light exposure was performed by placing the well plate under known LED light source. The given light intensity was analyzed with Thorlabs PM100D and S121C sensor head. Treatment time was changed to result in desired light amount.

CFU: After the exposure the biofilm was removed from the well by mechanically scraping it from bottom of the well plate using sterile inoculation rod. 100 µl of the resulting bacteria suspension was then plated on BHI-plate with different dilution rations between 1:1 to 1:10 000.

Tests and Results

The first experiment of continuous treatment of *Streptococcus* biofilm with PDT was completed by using 250 µg/ml ICG with 810 nm light. Different age biofilms of 1 day, 2 days and 4 days were grown, and the treatment was given once to each biofilm to evaluated the effect of single time treatment to differently aged biofilms.

In addition to these three tests, a 4 day old biofilm was grown that was exposed to PDT treatment every day. The initial hypothesis was that everyday treated biofilm would have close to zero CFU. The results of single wavelength treatment are shown in FIG. 10 which shows the efficacy of the PDT treatment on 1, 2 and 4 days old *Streptococcus mutans* biofilms. Two variants of 4 days old biofilm were done. One was exposed to PDT treatment every day and other only on a day 4.

The growth of total bacteria amount in controls as biofilm aged and the strong effect of PDT treatment to this biofilm model were as expected. The poor treatment effect in every day treated biofilm was surprising observation as it has been widely agreed that bacteria cannot develop resistance against photodynamic treatment. All of the above-mentioned experiments were repeated at least three times and 4 days every day treated biofilm was repeated 12 times to validate the finding.

A similar effect was not observed when a combination treatment was used. In this treatment the biofilm was targeted with combination of endo- and exogenous therapy. It was before shown in bacteria plate studies that 70 $J/cm^2$ amount of 405 nm light was needed to kill *Streptococcus mutans*. In dual combination experiment the red light (peak 810 nm) was combined with blue light (peak 405 nm). Multi light experiment focused to study the resistance inducing effect and thus it focused in 4 days old biofilm model with light treatment done daily and only on day 4. The hypothesis was that the everyday treatment would result in a poorest result as it was observed before. The experiment results are shown in FIG. 11.

FIG. 11 is a bar chart showing a 4 days old biofilms treated with double wavelength and single wavelength PDT system, respectively. No significant difference of bacteria killing between every day therapy and 4 days therapy was observed in double wavelength system where as the single wavelength PDT failed to achieve strong bacteria killing in continuous treatment.

The treatment with dual wavelength combination light was thus more effective and no bacteria biofilm adaptation to the treatment was observed.

Figure 6:
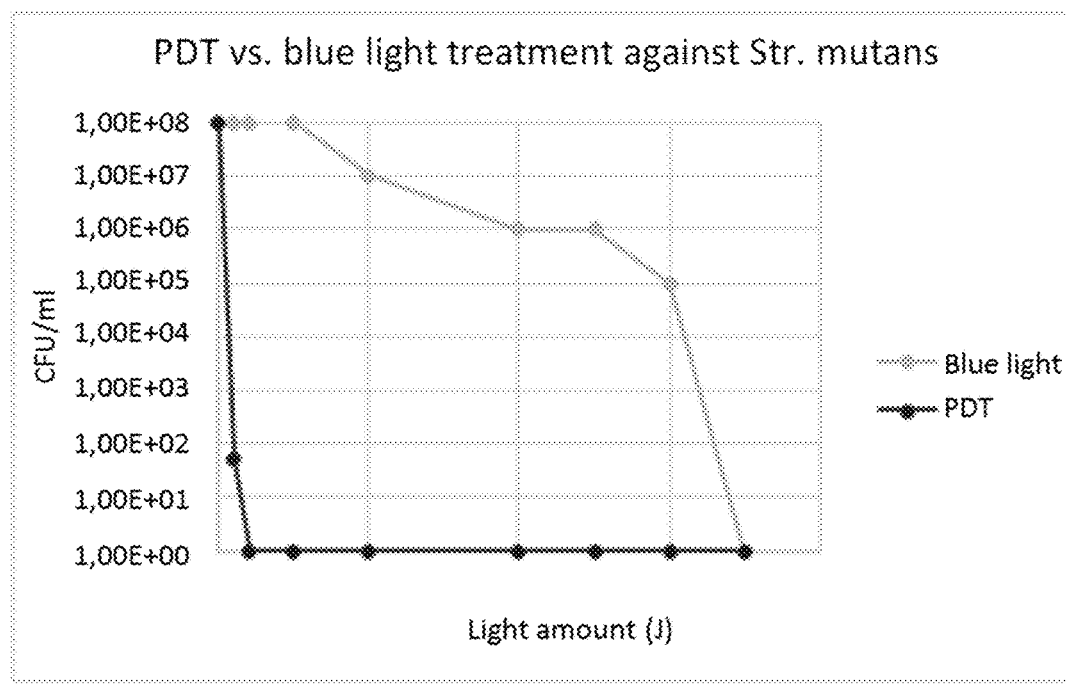
FIG. 6 is a chart showing the antibacterial effect of light having a wave length of 405 nm compared to PDT.

It would appear that a combination of endo- and exogenous photodynamic treatment simultaneously will increase the efficiency of biofilm targeted PDT. FIG. 6 shows the antibacterial effect of a treatment with 405 nm light compared to PDT.

As will appear from the figures, 405 nm light is not able to show strong effectivity against *Streptococcus mutans* until with high over 70 J/cm$^2$ energy density. For PDT the killing effect was much stronger. Already a dose of 4 J/cm$^2$ resulted in complete inhibition of *Streptococcus mutans* growth.

Finally it should be noted that in a fourth series of tests, similar results as above were obtained for treatment of Gram(−) bacteria.

Use of high and low energy photons with photosensitizer has better, more constant and robust antibacterial effect against gram positive and gram negative bacteria compared to traditional PDT which may lack effectivity against either gram negative or positive bacteria species as the different cell wall structures are susceptible for photosensitizers with different properties. Use of High and low energy photon treatment with active substance is recommended as it has minimal effect on the balance between gram negative and positive bacteria in the treatment area.

Figure 7:
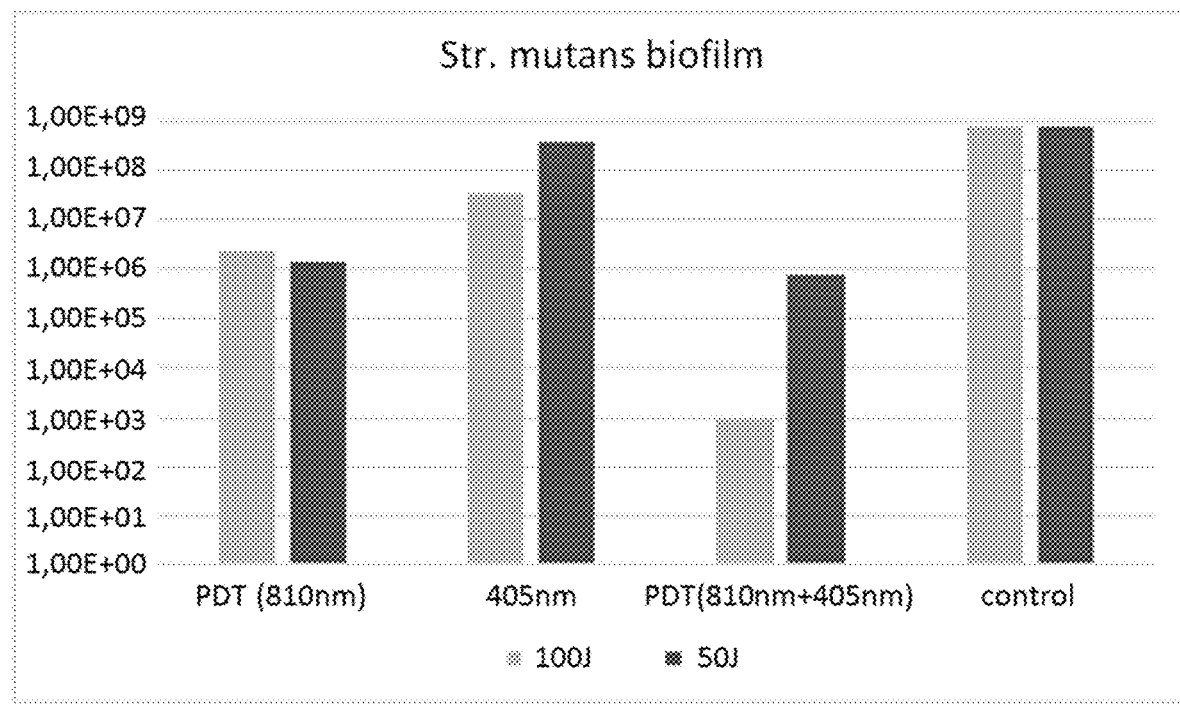
FIG. 7 is a bar chart showing the antimicrobial effect of PDT treatment after 14 days on *Streptococcus mutans* biofilms

FIG. 7 is a bar chart showing the antimicrobial effect of PDT treatment after 14 days on *Streptococcus mutans* biofilms. The left-hand bar of each pair represents the result of light treatment at 100 J and the right-hand bar represents the result of light treatment at 50 J (per cm$^2$). As will become apparent, the present light treatment proves to be highly efficient against microbes.

INDUSTRIAL APPLICABILITY

The present invention can be used for treatment of biological surfaces. In particular, the present a method can be used for treating surfaces. Biological surfaces are any surfaces, typically biological tissues and their surfaces, which are or can be subjected to biological contamination caused by of formed by micro-organisms. Such biological contamination is typically represented by biofilms and by biofilm infections, including dental infections caused by dental plaque, as well as dermal infections, urinary tract infections, middle-ear infections, endocarditis and implant- or catheter-associated infections. By the treatment, biological contamination of surfaces, such as microbial or viral or fungal contamination of biological tissues, can be prevented or combatted. The treatment can be used for cosmetic purposes as well as for antimicrobial and antiviral and antifungal therapy. Thus, generally, viral or fungal infections of tissue, in biofilm, saliva, skin, plaque, on teeth surfaces and in mucous membranes. The present treatment can also be used for treating other than biological materials having biological surfaces. Examples include equipment and part of equipment covered by biofilms. Such biofilms can be found generally in industrial water systems, in the medical and process industries, including the paper and pulp industry, as well as in the food industry.

The invention claimed is:

1. A method of treating biological surfaces comprising: treating a biological surface with chlorhexidine together with electromagnetic radiation in the form of light of two different energy levels, a first light with photons having a majority energy in the range from 3.17 eV to 2.95 eV and a second light with photons having a majority energy in the range from 1.56 eV to 1.45 eV, wherein the photons of the first light and the second light are simultaneously directed against the biological surface.

2. The method according to claim 1, wherein
non-coherent radiant light energy is generated at the two different energy levels, a first and a second energy level;
from the non-coherent radiant light energy, there is provided the first light having a wavelength corresponding to the majority energy of the first energy level, and the second light having a wavelength corresponding to the majority energy of the second energy level; and
the photons of the first light and the second light are then simultaneously directed against the biological surface.

3. The method according to claim 1, wherein biological material of the biological surface is subjected to endogenous and exogenous excitement so as to generate reactive oxygen singlets or reactive oxygen species, or both.

4. The method according to claim 1, wherein the method prevents or combats microbial or viral or fungal contamination of biological tissues.

5. The method according to claim 1, wherein the method is carried out for cosmetic treatment or antimicrobial or antiviral or antifungal therapy.

6. The method according to claim 1, wherein the first and second light are combined with at least one photosensitizer for treating the biological surface.

7. The method according to claim 6, wherein the at least one photosensitizer is provided for topical treatment of mammal tissue, and wherein said at least one photosensitizer is applied to a superficial part of the tissue and the superficial part thus treated is subsequently or simultaneously subjected to the first and second light.

8. The method according to claim 6, wherein the at least one photosensitizer is contacted with microorganisms on the biological surface by applying the at least one photosensitizer on the biological surface in the form of an aqueous solution, an alcohol containing solution, a hydrophilic gel, a hydrophobic gel, a hydrophilic polymer, a hydrophobic polymer or a paste, lotion, tape, tablet, plaster, or band-aid.

9. The method according to claim 6, wherein the at least one photosensitizer is selected from a natural photosensitizer, a synthetic photosensitizer, or a combination thereof, wherein the at least one photosensitizer is selected from the group consisting of hypericin, curcumin, phenalenone derivatives, Cercosporin, psoralen, xanthotoxin, Angelicin, alpha-Terthienyl, Phenylthepatriyne, THC, Cannabidiol (CBD), and combinations thereof, and wherein the synthetic photosensitizer is selected from the group consisting of RB (Rose Bengal), MB, Porphyrin derivatives, Curcumin derivatives, Methylene Blue, Indocyanine Green, Erythosine, Phenalenone derivatives, Fullerene derivatives, Xanthene derivatives, and combinations thereof.

10. The method according to claim 1, wherein the first light and the second light are applied in conjugation with at least one exogeneous photosensitizer, which can be activated with the photons of the second light.

11. The method according to claim 10, wherein the at least one photosensitizer comprises a first photosensitizer and a second photosensitizer, and wherein the process further comprises applying to the biological surface, during a first period of time, a first photosensitizer, and during a second period of time, a second photosensitizer, which is different from the first photosensitizer.

12. The method according to claim 11, wherein the first photosensitizer and the second photosensitizer are activated using the first light and the second light, respectively.

13. The method according to claim 1, wherein the biological surface is selected from the group consisting of tissues, biofilms, saliva, skin, plaque, teeth surfaces, and mucous membranes.

14. The method according to claim 1, wherein the photons of the first light are absorbed by endogenous molecules and the photons of the second light are absorbed by exogenous molecules, and wherein the photons of the first and second light are simultaneously emitted from an optoelectronic device.

15. The method according to claim 14, wherein the optoelectronic device is committed to emit the photons of the first light and the photons of the second light using feed-in voltage or current that is alternated or pulsed at 1 Hz to 1 GHz frequency independently from each other.

16. The method according to claim 14, wherein the optoelectronic device further comprises a detector to detect photo luminescence of the endogenous molecules and the exogenous molecules, or their photo decomposition side products.

17. The method according to claim 14, wherein the optoelectronic device comprises a plurality of semiconductor chips that are connected in series or in parallel, the chips exhibiting emission energy in the range of 2.48 eV and 1.24 eV and in the range of 3.5 eV and 2.8 eV, respectively.

18. The method according to claim 1, wherein the first light is directed towards the biological surface at a first wavelength from 400 to 430 nm, at a dosage of 1 to 120 J/cm$^2$, and with a power density of from about 10 to about 2500 mW/cm$^2$ for a period of time from 0.5 s to 120 min, and the second light is directed towards the biological surface at a second wavelength from 780 to 830 nm, at a dosage of 1 to 120 J/cm$^2$, and with a power density of from about 10 to about 2500 mW/cm$^2$ for a period of time from 0.5 s to 120 min.

19. The method of claim 1, wherein the majority energy of the photons of the second light is exactly half of the majority energy of the photons of the first light.

20. The method of claim 1, wherein the majority energy of the photons of the first light is 3.06 eV and wherein the majority energy of the photons of the second light is 1.53 eV.

21. A kit for treatment of biological surfaces, the kit comprising:
an optoelectronic device configured for simultaneously emitting a first light with high energy photons having a majority energy in the range from 3.17 eV to 2.95 eV and a second light with low energy photons having a majority energy in the range from 1.56 eV to 1.45 eV;
at least one photosensitizer which can be activated by at least either of the high energy and low energy photons; and
chlorhexidine.

22. The kit according to claim 21, wherein the optoelectronic device is configured to emit two wavelengths simultaneously or at a time interval of 0.001 to 1000 ms from each other.

23. The kit according to claim 21, further comprising a sensor capable of monitoring treatment progression, said sensor being capable of detecting treatment progression and of producing a regulation signal based on the progress of the treatment, said sensor being coupled to the optoelectronic device to adjust the first or second light emitted from the optoelectronic device depending on the regulation signal.

24. The kit according to claim 21, wherein the optoelectronic device comprises the shape of a tooth brush, or the shape of a mouth piece which can be inserted in a mouth of user between biting surfaces of the teeth, or the shape of a rod-like illuminator.

25. The kit according to claim 21, wherein the optoelectronic device comprises micro-spectrometer sensors, temperature sensors, light sensors, pH sensors, force sensors, gyroscopes, pressure sensors, or combinations thereof.

26. The kit according to claim 21, further comprising a tooth whitening substance capable of being used with the optoelectronic device or together with the at least one photosensitizer.

27. The kit according to claim 21, wherein the at least one photosensitizer is in form of water soluble effervescent tablet, and wherein the optoelectronic device comprises a hand held light applicator capable of emitting the first and second light.

28. The kit according to claim 21, wherein the at least one photosensitizer is in the form of a water soluble effervescent tablet, gel, or paste, and wherein the kit further comprises a one-time use mouth piece and a light applicator.

29. A method of treating biological surfaces comprising:
treating a biological surface with electromagnetic radiation in the form of light of two different energy levels, a first light with photons having a majority energy in the range from 3.17 eV to 2.95 eV and a second light with photons having a majority energy in the range from 1.56 eV to 1.45 eV,
wherein photons of the first light and the second light are simultaneously directed against the biological surface, and
wherein the energy intensity ratio between the first light and the second light is in the range of 5:1 to 0.2:1.

30. The method of claim 29, wherein the energy intensity ratio between the first light and the second light is in the range of 3:1 to 1:3.

31. The method according to claim 29, wherein the first and second light are combined with at least one photosensitizer for treating the biological surface.

32. A method of treating a biofilm comprising:
treating the biofilm with chlorhexidine along with electromagnetic radiation in the form of light of two different energy levels, a first light with photons having a majority energy in the range from 3.17 eV to 2.95 eV and a second light with photons having a majority energy in the range from 1.56 eV to 1.45 eV, wherein photons of the first light and the second light are simultaneously directed against the biofilm,
wherein the first and second light are combined with at least one photosensitizer for treating the biofilm, and wherein the at least one photosensitizer comprises Indocyanine Green.

33. A kit for treatment of biological surfaces, the kit comprising:
an optoelectronic device configured for simultaneously emitting a first light with high energy photons having a majority energy in the range from 3.17 eV to 2.95 eV and a second light with low energy photons having a majority energy in the range from 1.56 eV to 1.45 eV, wherein an energy intensity ratio between the first light and the second light is in the range of 5:1 to 0.2:1; and
at least one photosensitizer which can be activated by at least either of the high energy and low energy photons.

\* \* \* \* \*